United States Patent [19]

Emerson

[11] Patent Number: 5,553,324
[45] Date of Patent: Sep. 10, 1996

[54] GRIPPING AID

[76] Inventor: Samuel J. Emerson, 2209 2nd St., White Bear Lake, Minn. 55110

[21] Appl. No.: 312,560

[22] Filed: Dec. 1, 1994

Related U.S. Application Data

[63] Continuation-in-part of Ser. No. 136,706, Oct. 15, 1993, abandoned.

[51] Int. Cl.$^6$ .......................... A41D 13/08; A41D 19/01
[52] U.S. Cl. .................. 2/158; 2/161.1; 2/161.4; 2/161.6; 2/917; 602/64
[58] Field of Search ............... 2/159, 161.2, 161.4, 2/162, 16, 160, 161.1, 161.6, 161.7, 910, 917, 170, 920, 158; 602/21, 20, 62, 64; 128/879; 273/188 R, 189 R

[56] References Cited

U.S. PATENT DOCUMENTS

| | | | |
|---|---|---|---|
| 2,083,604 | 6/1937 | Hay | 2/159 |
| 2,559,788 | 7/1951 | Patterson | 2/162 |
| 2,852,779 | 9/1958 | Roessler | 2/161 |
| 3,105,972 | 10/1963 | Christopher | 2/161 |
| 3,348,238 | 10/1967 | Hydock | 2/161 |
| 3,476,108 | 11/1969 | Matukas | 2/16 |
| 3,559,212 | 2/1971 | Skovron | 2/161.4 |
| 3,774,242 | 11/1973 | Owen | 2/16 |
| 4,400,831 | 8/1983 | Rietz | 2/161.1 |
| 4,584,993 | 4/1986 | Nelson | 602/21 |
| 4,643,428 | 2/1987 | Churchhill | 273/166 |
| 4,698,850 | 10/1987 | Patton, Sr. et al. | 2/161.1 |
| 4,730,354 | 3/1988 | Saito | 2/161 |
| 4,752,075 | 6/1988 | Bencriscutto | 273/183 B |
| 4,793,005 | 12/1988 | Hetzel, Jr. | 2/162 |
| 4,888,830 | 12/1989 | Putnam | 2/920 |
| 5,022,094 | 6/1991 | Hames et al. | 2/161.1 |
| 5,033,120 | 7/1991 | Myers | 2/161 |
| 5,088,122 | 2/1992 | O'Toole | 2/161 |
| 5,350,343 | 9/1994 | DaSilva | 2/20 |
| 5,414,868 | 5/1995 | Crawford | 2/160 |

FOREIGN PATENT DOCUMENTS

| | | | |
|---|---|---|---|
| 353055 | 1/1909 | France | 2/16 |
| 1021800 | 2/1953 | France | 2/16 |

*Primary Examiner*—Amy B. Vanatta
*Attorney, Agent, or Firm*—Haugen and Nikolai, P.A.

[57] ABSTRACT

A support aid permitting an individual with a weak wrist and hand to hold an object. The aid helps achieve a fist-like grasp about an object, without increasing pain. A sufficiently wide wrist band is provided to support a weakened wrist, wherein a hand strap extends therefrom to wrap about one's hand to form a fist and be secured to the opposing side of the hand strand. The aid can be implemented by one hand, which may also have reduced hand and wrist capabilities. Loops and rings are implemented to help one grasp and adjust the straps while adapting to one's hand. Utensils and equipment, such as pencils and golf clubs, can then be securely grasped and utilized.

9 Claims, 10 Drawing Sheets

GRIPPING AID

CROSS-REFERENCE TO RELATED APPLICATION

This application is a continuation-in-part of patent application Ser. No. 08/136,706, filed on Oct. 15, 1993, now abandoned, entitled "GRIPPING AID", the benefit of the filing date from this application now being claimed for common subject matter.

FIELD OF THE INVENTION

The present invention is generally related to a device which enables a person with a weak, injured or missing hand to securely hold an object such as a golf club.

Background of the Invention

Securely holding an object in one's hand can be a difficult task for those with a weakened hand or wrist. What may be an easy task for most individuals is often taken for granted. Those partially disabled and suffering from arthritis, carpal tunnel syndrome and muscle damage find gripping items to be a strenuous or unachievable task without assistance. Similarly, people with missing fingers (or even a missing hand) require the ability to grip objects as part of normal daily life. Such conditions make it impossible for such people to participate in recreational activities such as the game of golf.

Gripping a golf club shaft is one such task that such individuals require assistance. Some prior art devices known to assist those with a healthy hand are known to be disclosed in U.S. Pat. No. 5,088,122 to O'Toole; U.S. Pat. No. 4,643,428 to Churchill; U.S. Pat. No. 4,752,075 to Bencriscutto; U.S. Pat. No. 4,730,354 to Sarto; U.S. Pat. No. 3,105,972 to Christopher; U.S. Pat. No. 3,348,238 to Hydock; and U.S. Pat. No. 5,033,120 to Myers. These patents fail to teach a device which supports both the hand and wrist of an individual while holding an object, especially an individual with torn cartilage, carpal tunnel syndrome, missing fingers, or other similar disability.

OBJECTS

It is accordingly a principal object of the present invention to provide a device for use by persons with an injured or missing hand to securely hold an object.

It is a further object of the present invention to provide the ability to hold an object securely in one's hand among victims of accidents, illnesses, and birth defects.

Still a further object of the present invention is to provide a reversible gripping aid will enable a person with hand or wrist weakness to use the weak hand, and perform a variety of activities including, but not limited to, housework, gardening, carpentry, and sports activities such as fishing, hunting, archery, tennis, golf and skiing with confidence.

Another object of the present invention is to provide a device which is simple and inexpensive to construct.

Still yet a further object of the present invention is to provide a device that is easy to apply and secure to an operative position and which is easily removed after use.

SUMMARY OF THE INVENTION

The foregoing objects of the present invention are achieved by providing a device consisting of an elastic material which supports one's wrist and forms a pocket tightly over the knuckles of a fisted hand to create a solid hand grip. The device helps attain a secure grip of an object, such as a golf shaft.

In one preferred embodiment of the present invention, the device comprises an elongated elastic wrist band having a width of approximately two inches to sufficiently support a wrist when worn thereabout. The ends of the wrist band are joined together by a hook and loop type closure attached to both an upper and lower planar surface of the wrist band. The device further includes a gripping band made of elastic. The gripping band is sewn at one of its ends to the midsection of the wrist band. This gripping band is configured to be wrapped around either the left or right hand and/or the object to be held. The free end of the gripping band can be selectively secured to the wrist band with a hook and loop type closure (attached at the free end to both an upper and lower planar surface of the gripping band) after being tightly wrapped about the hand and/or object.

In an alternative embodiment, the wrist band is made of an elastic material having first and second ends. Sewn to the first end is an oval or rectangular shaped ring member through which the second end of the wrist band can be slidably received. The second end of the wrist band is passed through the oval shaped ring, a D-shaped ring is sewn to the second end of the wrist band. When used, the wrist band is slid over the wrist. The wrist band can then be pulled tight by using the D-shaped ring. A hook and loop type closure attached to both an upper and lower planar surface of the wrist band is used to hold the wrist band tight. This alternative embodiment also includes a gripping band sewn at one of its ends to the wrist band. The free end can then be pulled around the hand and/or object to be gripped and secured to the wrist band by a hook and loop type closure (attached at the free end to both an upper and lower planar surface of the gripping band).

DESCRIPTION OF THE PREFERRED EMBODIMENT

Figure 1:
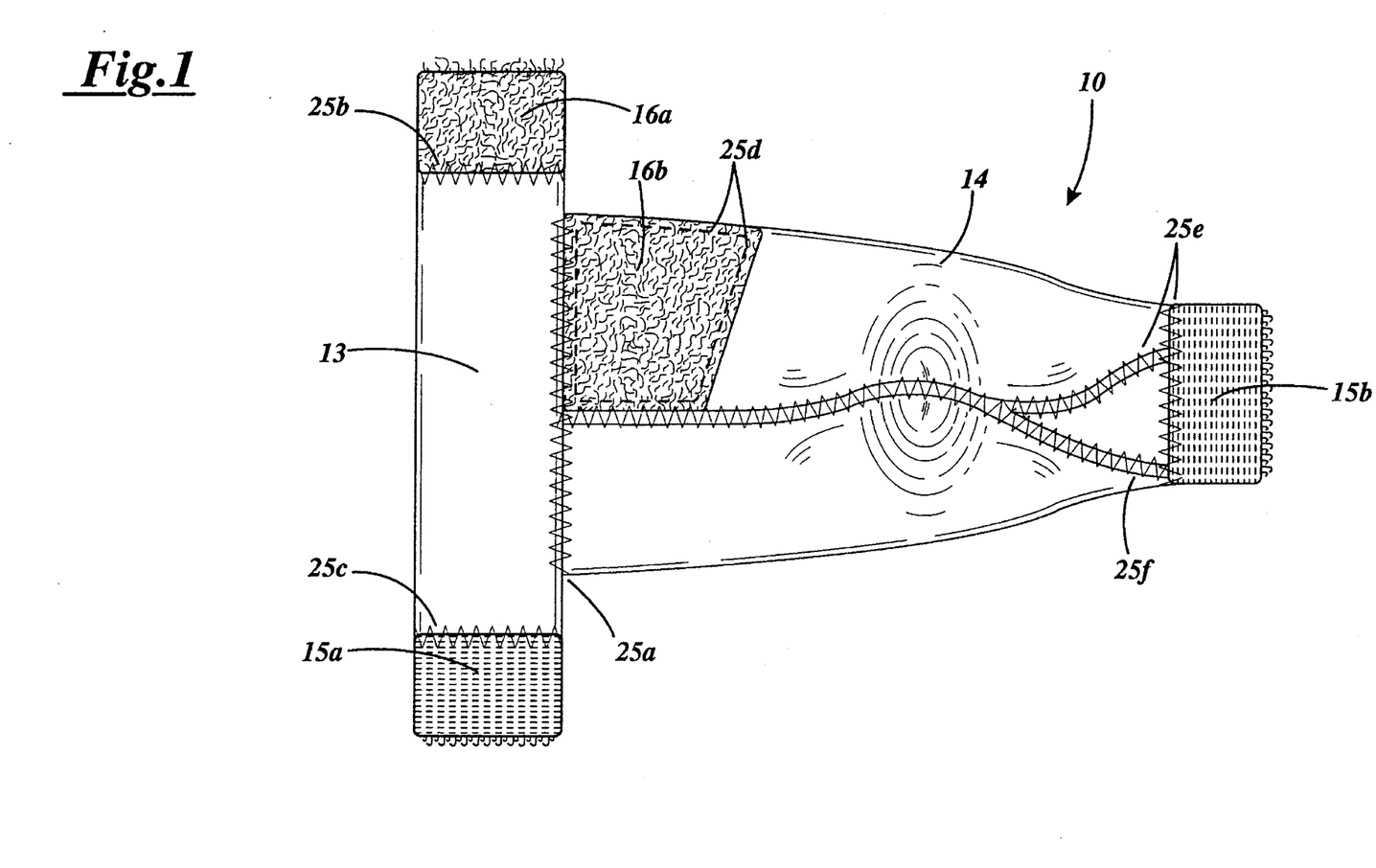
FIG. 1 is a top view of a hand and wrist supporting device comprised of a generally "T"-shaped composition of elastic material, wherein a Velcro® hook and loop arrangement is provided to secure the opposing end of the hand band to the wrist band.

Referring now to FIG. 1, a hand and wrist support device is generally shown at 10. Device 10 is comprised of two key elements: an elongated wrist band 13, and a generally trapezoidal-shaped elastic gripping band 14. One end of gripping band 14 is fastened by stitching at 25(a) to a mid-section of wrist band 13. Gripping band 14 extends generally perpendicular from, but at a slight angle from, wrist band 13.

Figure 2:
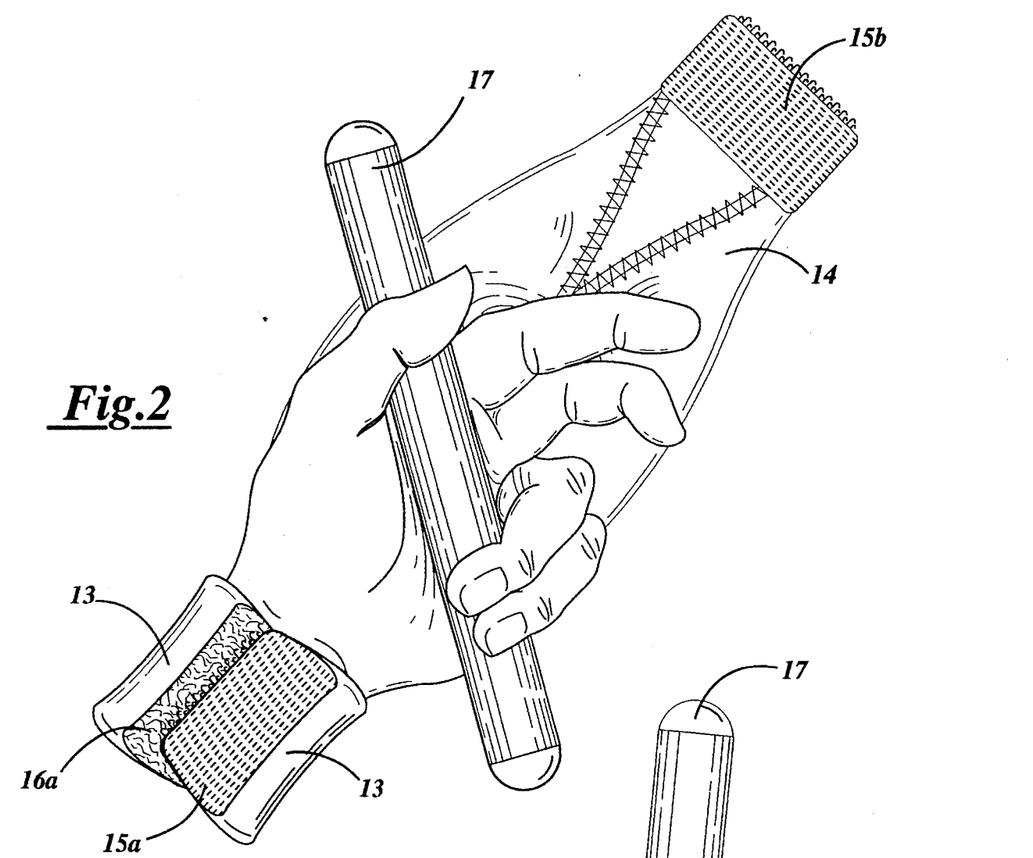
FIG. 2 is an illustration of a wearer's palm with an object in the hand in preparation for making a fist.
Figure 3:
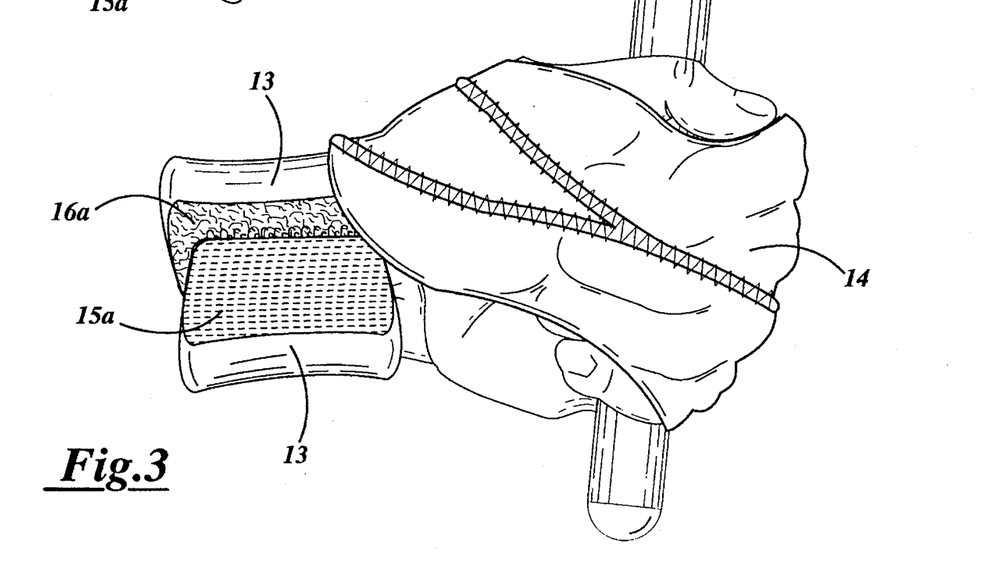
FIG. 3 illustrates the wrist band securely in place with the hand band securely brought over the palm and all four of the user's fingers to enable the user to grasp the object.
Figures 4, 5:
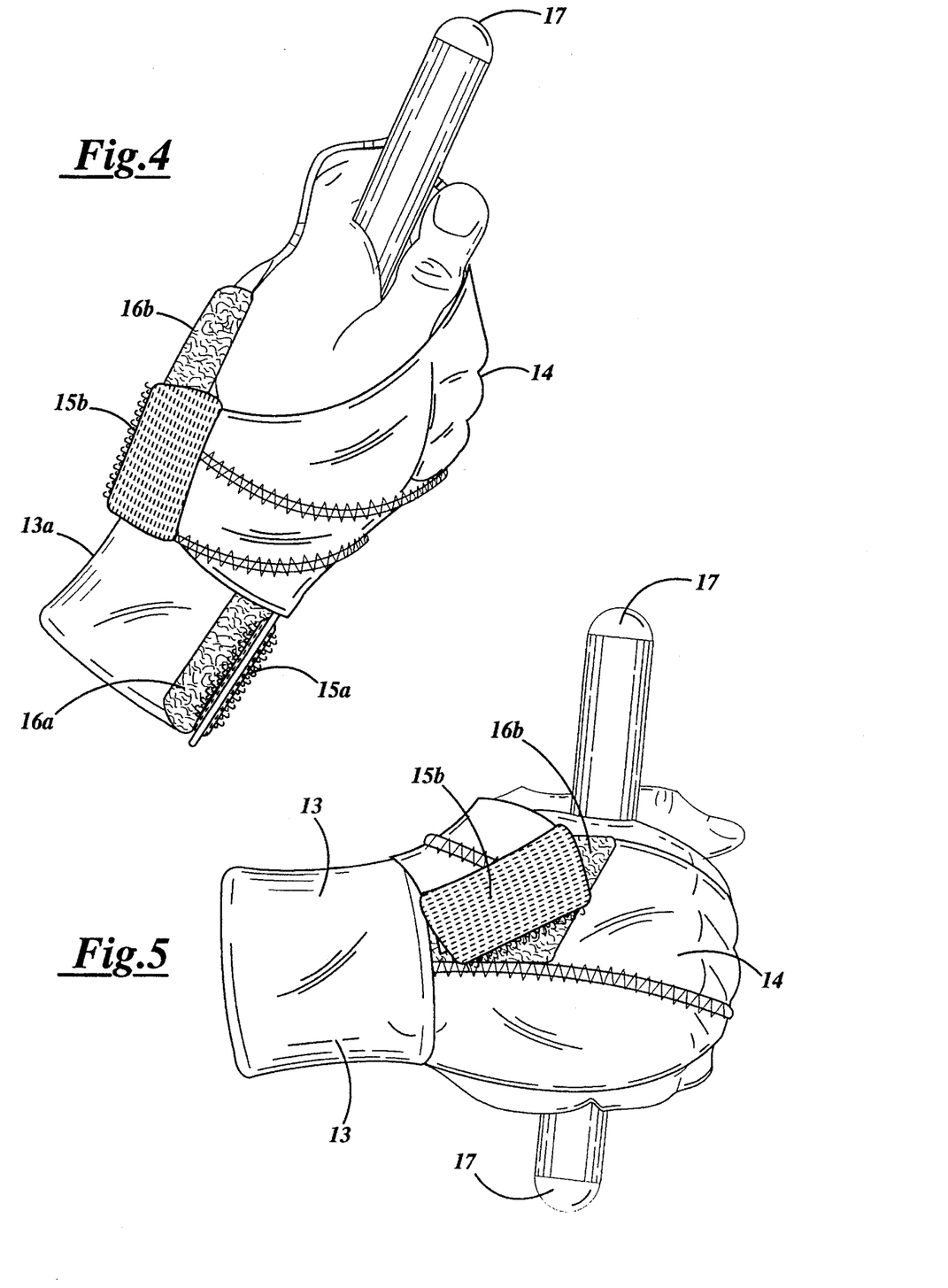
FIG. 4 is a back view of the hand shown in FIG. 3 illustrating the hand being encompassed by the hand band, with the hand band fastened back to itself on the back of the hand by the hook to the loop.
FIG. 5 is a top view of the wrist band securely fastened about the wearer's wrist, with the hand band surrounding all of the wearer's four fingers and attaching behind the exposed thumb to facilitate firmly holding the object in one's hand.

Stitched to opposing ends of wrist band 13 are pads 15a and 16a. Pad 15a includes a plurality of hooks and pad 16a includes a plurality of loops. Together, pads 15a and 16a form a hook and loop type closure. This arrangement permits the wrist band 13 to be drawn around and secured about a wearer's wrist. The free end 15b of gripping band 14 is also provided with a pad of hooks. These hooks are adapted to be secured to a pad of loops 16b also provided on gripping band 14 adjacent wrist band 13. Gripping band 14 is formed of a plurality of elastic segments each secured to one another by stitching 25d, 25e and 25f. When used, gripping band 14 is wrapped around the hand and/or object to be gripped as shown in FIGS. 2–5, wherein the pad of hooks 15a and 15b and pad of loop 15a and 16b are attached to both the upper and lower surface of the gripping aid 10 as shown in FIG. 2. FIGS. 2–4 show the device wrapped around a left hand, whereas FIG. 5 shows the device reversed and wrapped around a right hand. The hooks on pad 15 are then joined with the loops of pad 16a to form a hook and loop type closure. As indicated above, such hook and loop type closures are often referred to as Velcro®.

Referring to FIG. 2, device 10 is seen to be attached to one's hand by first securing wrist band 13 about the wearer's wrist using pads 15a and 16a. Wrist band 13 is particularly characterized as having a width dimension of approximately two inches or more to provide adequate support to the wearer's weakened wrist. An object 17, such as the shaft of a golf club, is placed in the palm of the wearer's hand and under the wearer's thumb. Next, the free end of gripping strap 14 is tightly wrapped about the fingers and knuckles of the hand to form a fist, allowing the individual to grip object 17. Referring to FIG. 3, gripping strap 14 can be seen to be wrapped over the fingers and palm of one's hand with the wearer's fingers being shown in phantom thereunder. Referring to FIG. 4, the pad of hooks of pad 15b at the free end of gripping strap 14 can be seen to be secured to the loops of pad 16b. Gripping strap 14 maintains a snug fit about the closed hand, and helps one maintain a secure grip of object 17. In that both wrist band 13 and gripping band 14 are composed of elastic materials, the device is comfortably worn. FIG. 5 shows a top view of the right hand secured about the object 17, wherein the wrist is supported by the wide 2-inch wrist band 13.

Figure 6:
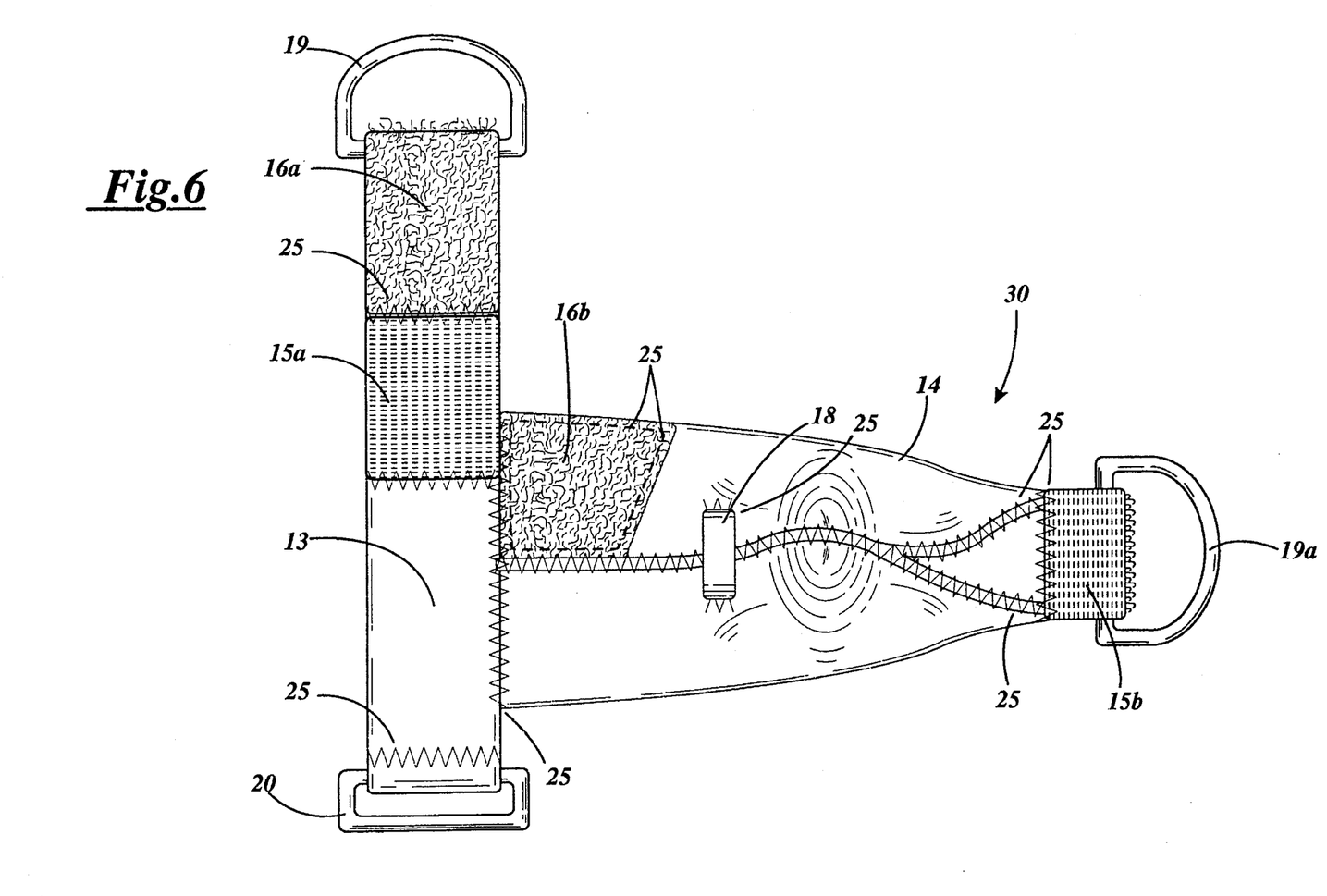
FIG. 6 is a top view of an alternative preferred embodiment whereby the elastic wrist band is provided with a rectangular loop at one end, and "D"-shaped ring at the other end.

Referring now to FIG. 6, an alternative preferred embodiment of the present invention is shown at 30. This embodiment also includes a wrist band 13 and a gripping band 14. Sewn to one end of wrist band 13 is a rectangular shaped ring 20. Sewn to the other end of wrist band 13 is a D-shaped ring 19. Located immediately adjacent each other on each side of wrist band 13 are a pad of hooks 15a and a pad of loops 16a (see FIGS. 6 and 7). When in use, the wrist band 13 is drawn around the wearer's wrist, the D-shaped ring 19 is slipped through the rectangular shaped ring 20, and the user pulls back on the D-shaped ring 19 to adjust the tightness and, thus, the support provided by the band. When this is done, pads 15a and 16a are placed in face-to-face registration and can be joined together to secure the wrist band 13 in place. As shown in alternate preferred embodiments in FIGS. 8, 10, and 12, the position of the D-shaped ring 19 and the rectangular shaped ring 20 on each end of the wrist band 13 may be opposite that shown in FIG. 6. Likewise, the pad of hooks 15 and pad of loops 16 are shown in FIGS. 7, 8, 10, and 12 in alternate positions on the wrist band 13 from the positions shown in FIG. 6.

Figure 7:
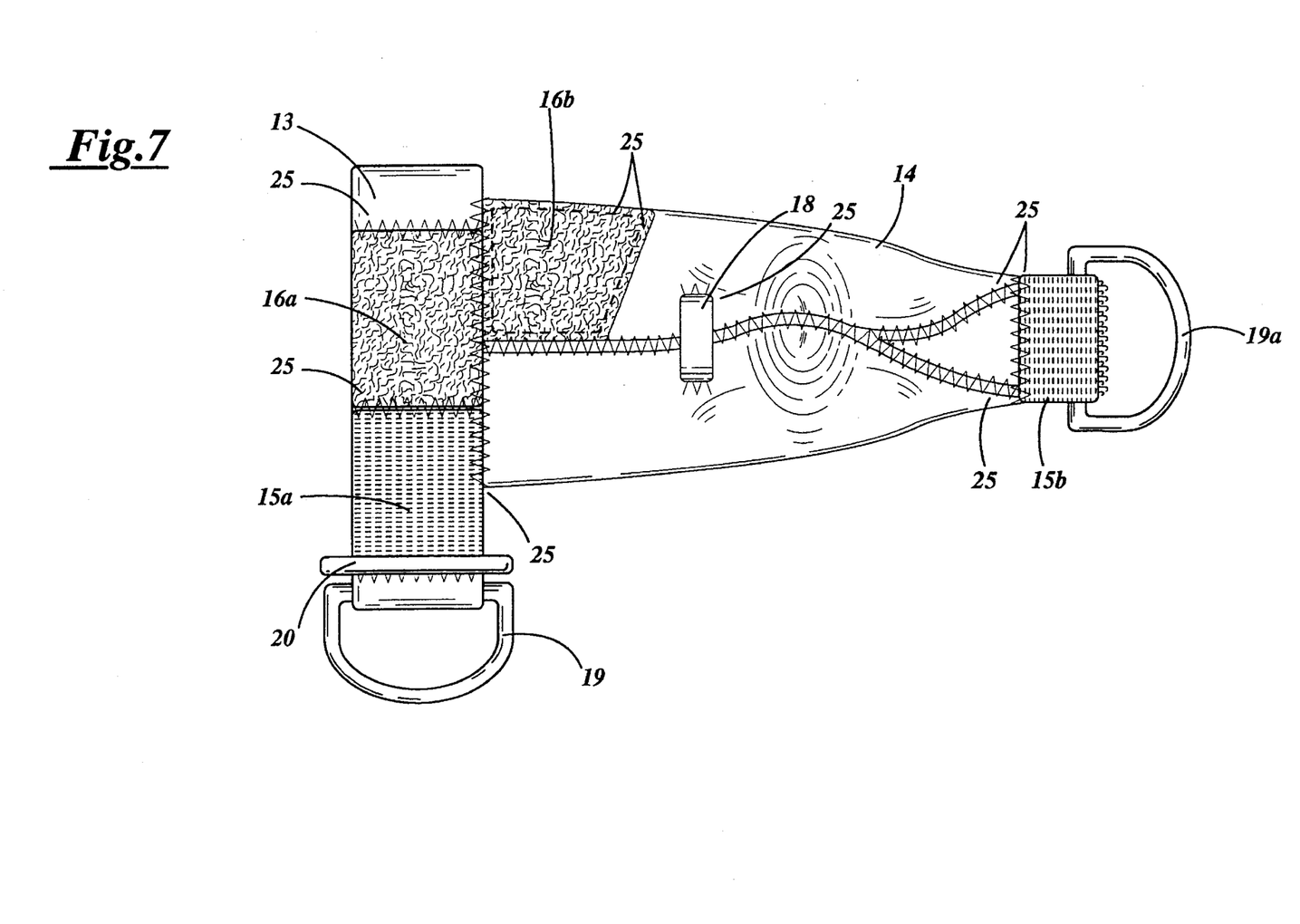
FIG. 7 details the "D"-shaped ring of an alternate preferred wrist band being threaded and pulled through the rectangular loop in preparation of folding back thereover.
Figure 8:
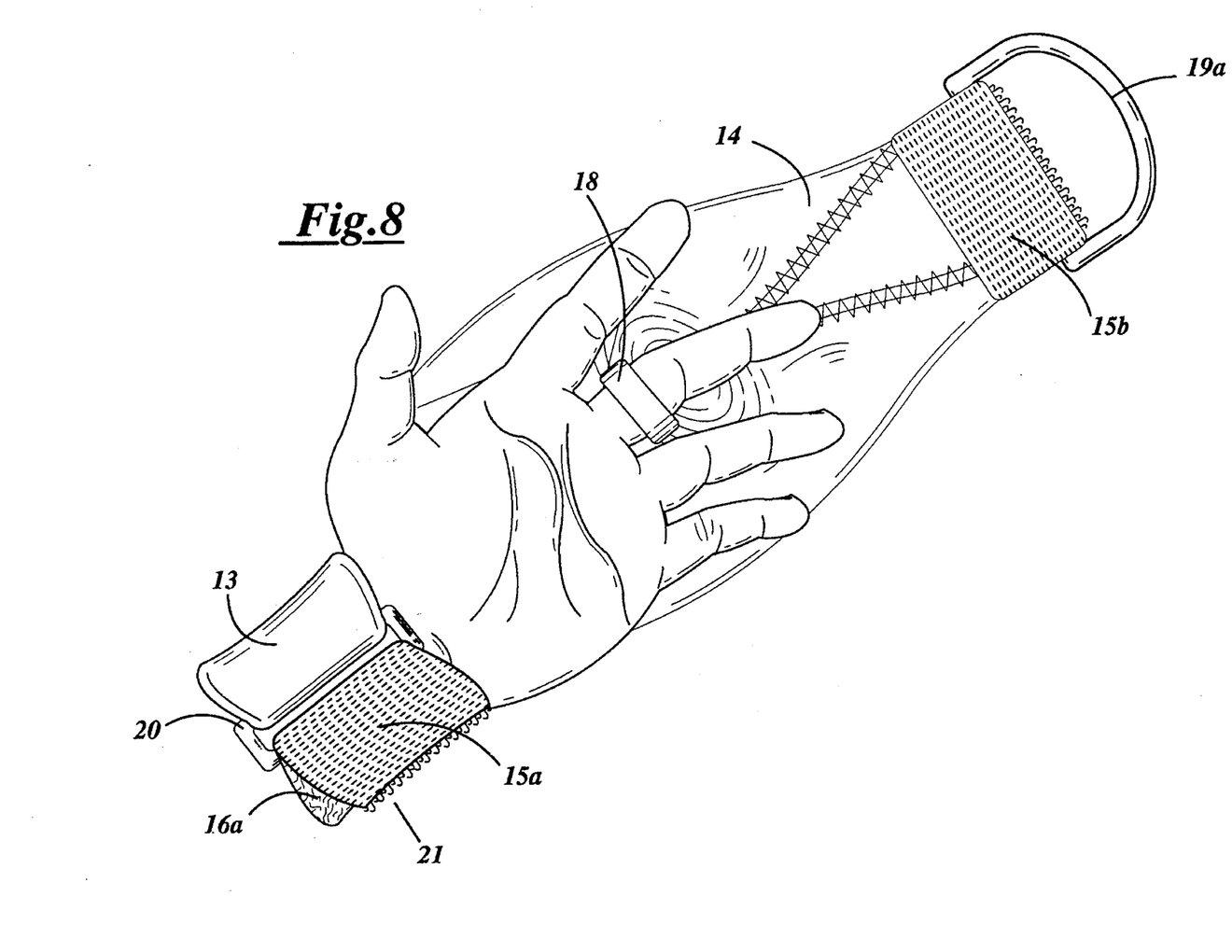
FIG. 8 shows the palm of the wearer's hand with the middle finger inserted in a loop provided on the inside surface at the mid-section of the hand band, prior to the distal end of the hand band being folded tightly about the knuckles of a closed fist having an alternate preferred wrist band.
Figure 9:
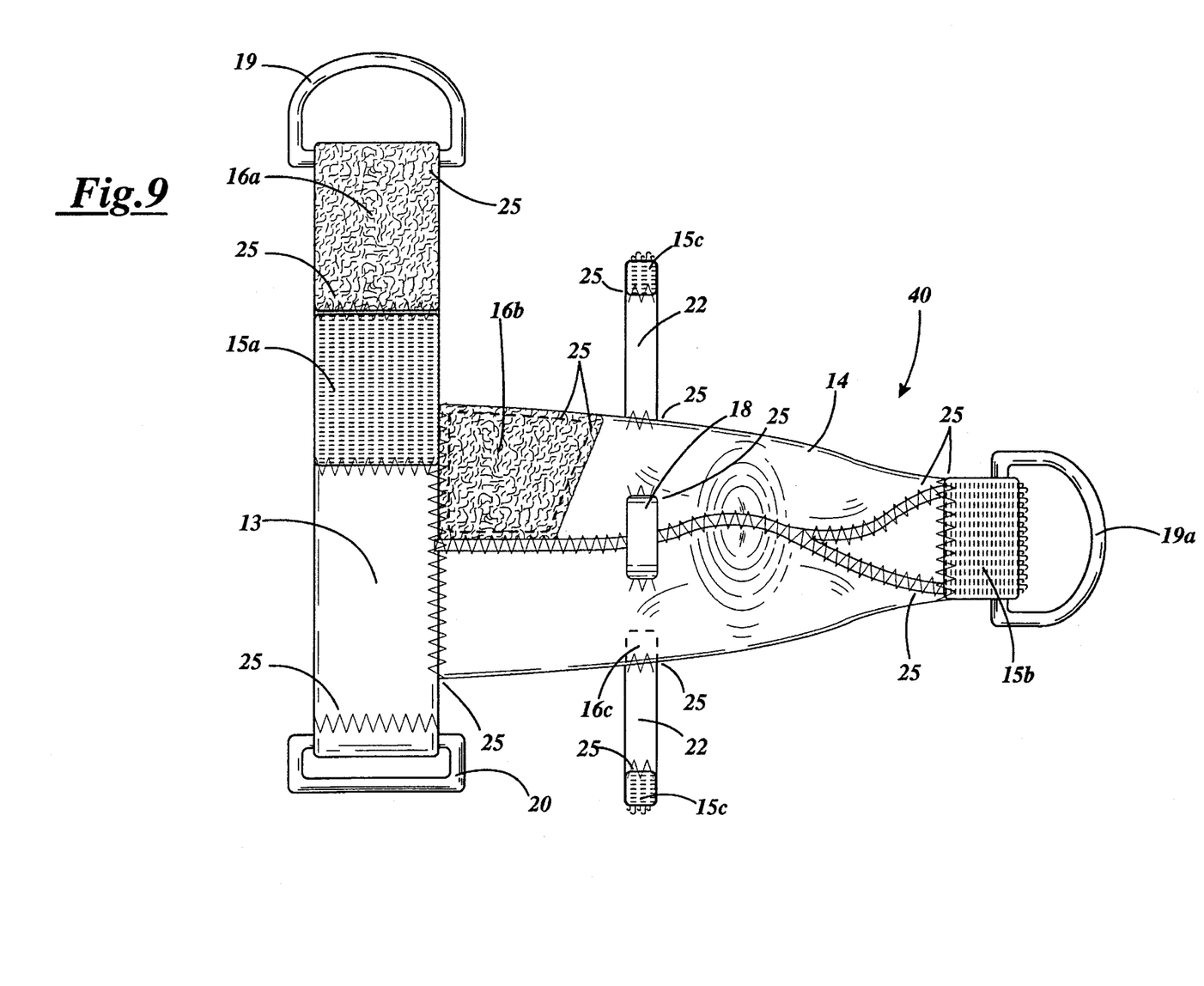
FIG. 9 is yet another alternative preferred embodiment of the invention shown in FIG. 6, whereby a pair of opposing elastic stabilizer strips are sewn to the upper and lower mid-section of the hand band, proximate the loop receiving the middle finger.
Figure 10:
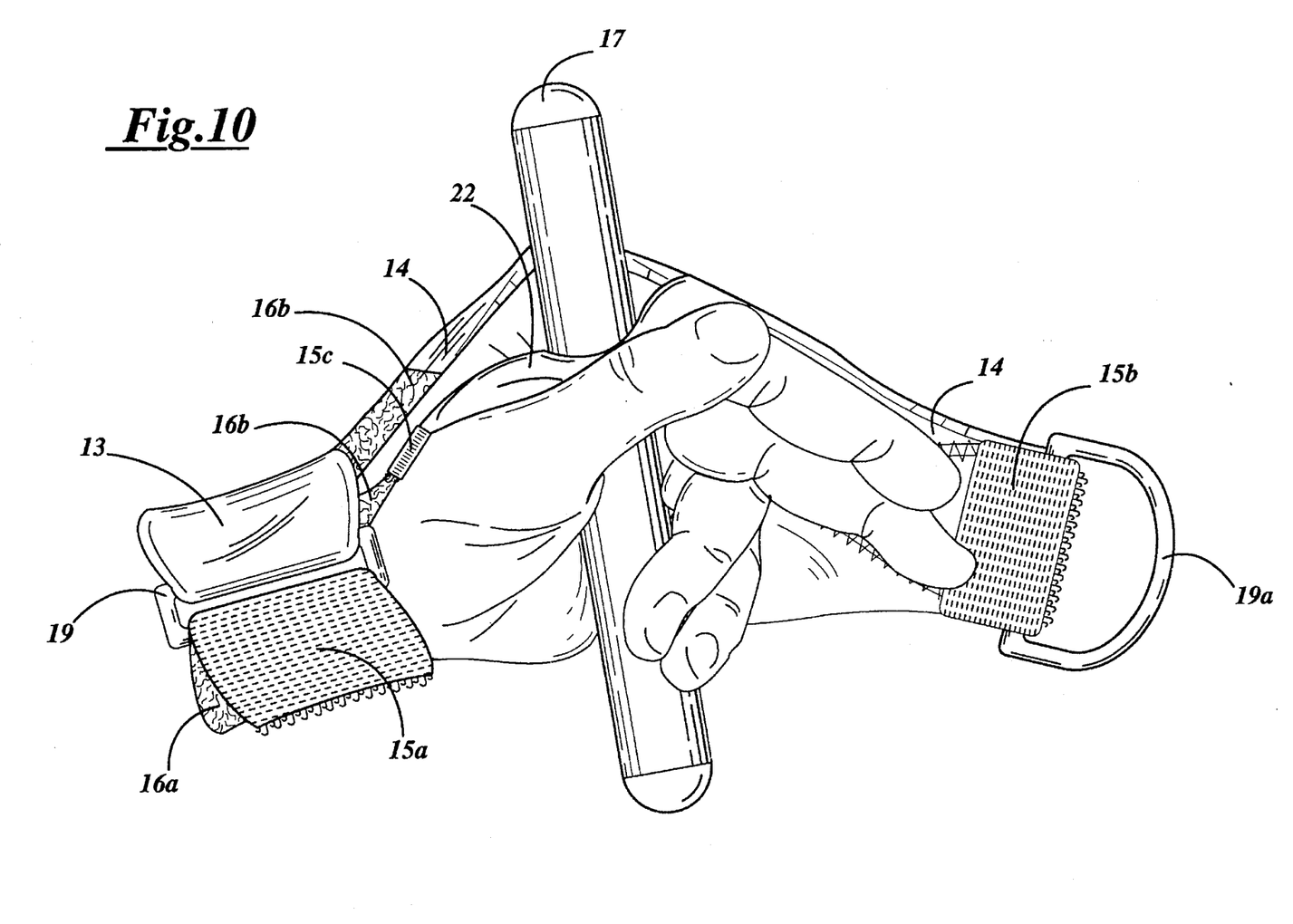
FIG. 10 is a top view of the gripping band of FIG. 9 having an alternate preferred wrist band adapted to a wearer's hand starting to encircle an object, whereby one stabilizer strip is attached to the wrist band to help position the object while the hand band is subsequently secured about the hand.

The gripping band 14 may have the same design as that described with respect to the first preferred embodiment. Alternatively, it may have one end stitched to the wrist band 13 and the free end stitched to a D-shaped ring 19a. D-shaped ring 19a is used as a handle to pull the gripping band 14 around the hand or object to be held. As shown in FIGS. 6–8, the gripping band 14 may also have one or more finger loops, such as 18, stitched to it. Such finger loops can serve to properly orient the gripping band 14 when a finger is inserted through the loop. The gripping band of this embodiment also includes a hook and loop type closure 15b and 16b (attached at the free end to both an upper and lower planar surface of the gripping band 14) like the gripping band of the first preferred embodiment Referring now to FIG. 9, the embodiment of FIG. 6 is further shown at 40 with a pair of opposing stabilizer strips 22 being sewn to (and extending from) opposing sides of gripping band 14. These stabilizer strips are located proximate the finger-securing loop 18, as shown. At the free end of each strip 22 is provided a hook pad 15c. Referring to FIG. 10, the pad 15c of each stabilizer strip 22 is used to releasably secure the free end of the strip 22 to loop pad 16b of gripping strap 14 to help stabilize object 17 within the wearer's palm. This is usually done prior to securing hand strap 14 about the hand to form a fist.

Figure 11:
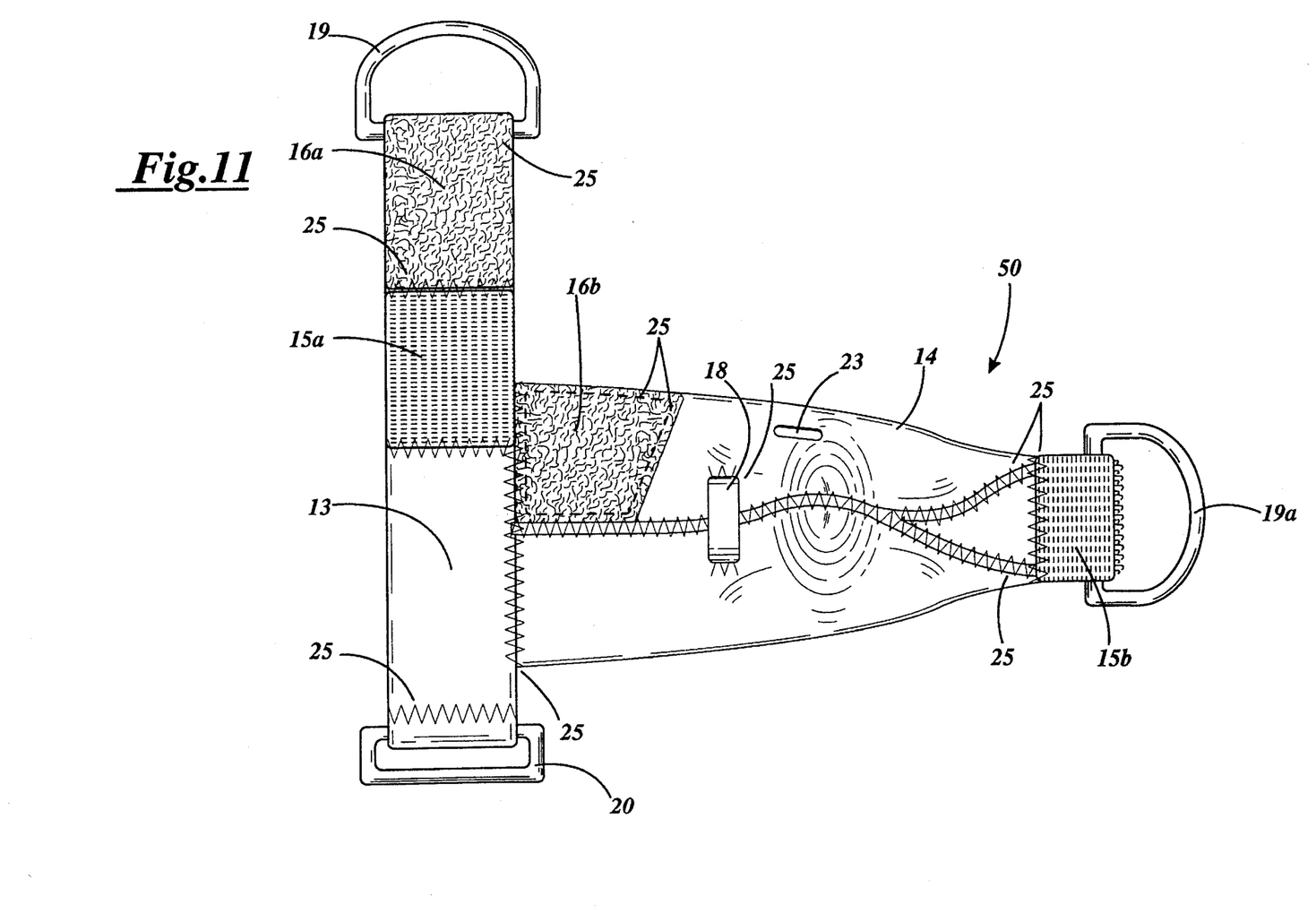
FIG. 11 is another alternative embodiment of the present invention whereby the upper portion of the hand band is slit to permit a writing utensil or similar object to be inserted through it.
Figure 12:
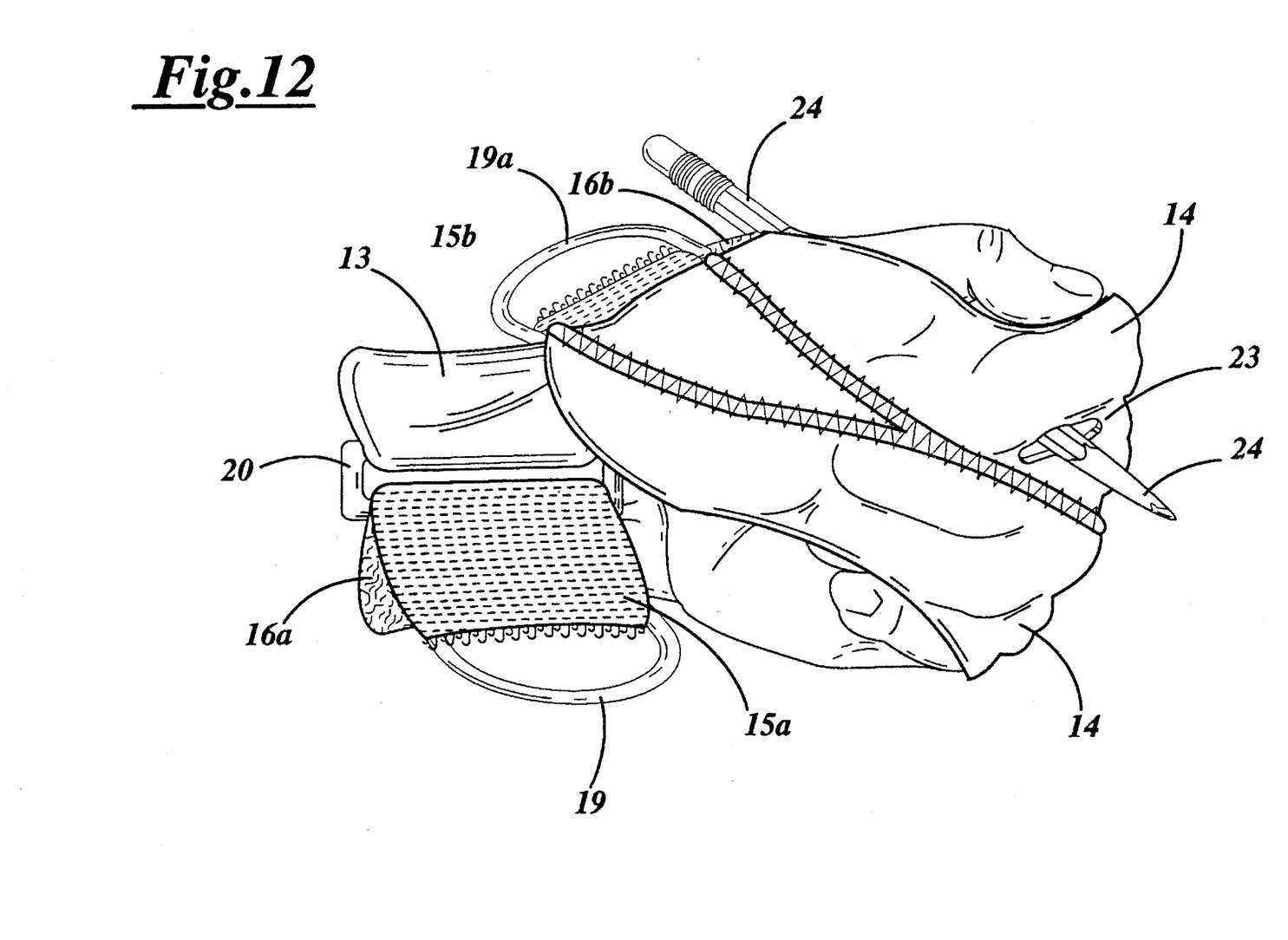
FIG. 12 is a top view of the wearer's hand having an alternative preferred wrist band and hand band of the type shown in FIG. 11 attached thereto to securely hold the object firmly in one's hand after being placed through the slit.

Referring now to FIG. 11, the embodiment of FIG. 6 is further shown at 50 to include a slit 23 provided at the midsection of hand strap 14. Slit 23 permits a writing tool, eating utensil or similar object to be inserted through it. Referring to FIG. 12, a top view of the wearer's hand with the wrist band 13 and gripping band 14 secured thereabout is shown, wherein the object is firmly held in the hand after the object has been placed through slit 23 of gripping band 14.

Each of the various embodiments of the present invention provide two functions. First, the wrist band 13 is sufficiently wide to support the wearer's weakened wrist. Secondly, the gripping band 14 can be tightly wrapped about a wearer's knuckles and fingers to close and maintain a tight fist about a held object. The resulting dual function helps one with a weak hand and wrist to perform certain functions such as holding utensils and objects, such as golf clubs.

The present invention is particularly designed to be easily used by individuals with such reduced capabilities of the wrist and hand. The wrist bands of FIGS. 1 and 6 can be easily attached and secured about one's wrist with one hand, even if the wearer has limited use of one's hand. The particular embodiment of FIG. 6, as shown in FIG. 7, includes a wrist band which is always formed in a loop. The wrist band can be secured to one's wrist after the hand has been inserted through the wrist band loop by subsequently grasping and folding the wrist band "D"-shaped ring 19 back over rectangular loop 20, wherein the wrist band pad 15a is then secured to pad 16a to one's comfort level (See FIG. 7). In this embodiment, one simply needs to grasp "D"-ring 19, pull tight, and fold pad 15a thereover to be secured to pad 16a. No lining up of opposing wrist strap ends is required. The "D"-shaped ring 19a at the free end of gripping band 14 is also easily secured about the fisted hand, and back to itself at pad 16b by simply grasping the "D"-shaped ring 19a.

In summary, the present invention is particularly designed to be implemented using only one hand, which too may be weakened. The device is simple and easy to manufacture, implementing well known articles and only a modest amount of stitching. Finger loop 18 and stabilizer straps 22 permit additional orientation capabilities which will be appreciated by those with limited use of their hands and wrists.

This invention-has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A device for supporting a wearer's hand and wrist, comprising:

(a) an elongated elastic wrist band having a width of at least two inches to sufficiently support the wearer's wrist when worn; and (b) an elastic gripping band which extends around the knuckles of the hand, said gripping band being coupled to a mid-section of said wrist band and extending therefrom to a free end, said free end including first securing means for selectively securing said free end back to second securing means, located on said gripping band adjacent to both the wrist band and a lateral edge of said gripping band, after the gripping band has been firmly wrapped around the wearer's hand holding an object to be gripped.

2. The device as specified in claim 1 wherein said wrist band has a first end and a second end, the first end having a third securing means and the second end having a fourth securing means which can be joined together for selectively securing the first and second ends of the wrist band together after the wrist band is wrapped around the wearer's wrist.

3. The device as specified in claim 2 wherein said wrist band further includes a first ring member secured to the first end and a second ring member secured to the second end, said first ring member being of a size to slidably receive the second end of said wrist band so that the second ring member can be used to tighten the wrist band about the wrist before the said third and fourth securing means are joined together to selectively secure the first and second ends of the wrist band together.

4. The device as specified in claim 3 wherein said second ring member is D-shaped.

5. The device as specified in claim 2 or claim 3 wherein said first and third securing means each comprise a pad consisting of a plurality of hooks, and said second and fourth securing means each comprise a pad consisting of a plurality of loops, such that said first and second securing means form a hook and loop type closure and said third and fourth securing means also form a hook and loop type closure.

6. The device as specified in claim 1 wherein the free end of said gripping band has a D-shaped ring attached to it.

7. The device as specified in claim 1 wherein said gripping band also includes at least one finger receiving loop secured thereto.

8. The device as described in claim 1 further including a slit through said gripping band for receiving an elongated object to be gripped.

9. The device as described in claim 1 further including a pair of stabilizer strips, each said strip being sewn at one end to said gripping band and having means for releasably securing the other end to the gripping band or the wrist band after said stabilizer strip is wrapped about an item to be gripped.

* * * * *